US00PP18905P2

(12) United States Plant Patent
Lintott

(10) Patent No.: US PP18,905 P2
(45) Date of Patent: Jun. 10, 2008

(54) *CHRYSANTHEMUM* PLANT NAMED 'MERMAID YELLOW IMPROVED'

(50) Latin Name: *Chrysanthemum morifolium*
Varietal Denomination: Mermaid Yellow Improved

(75) Inventor: Keith G. Lintott, Bognor Regis (GB)

(73) Assignee: Cleangro Ltd., Chichester, West Sussex (GB)

( * ) Notice: Subject to any disclaimer, the term of this patent is extended or adjusted under 35 U.S.C. 154(b) by 0 days.

(21) Appl. No.: 11/698,349

(22) Filed: Jan. 26, 2007

Related U.S. Application Data

(60) Provisional application No. 60/763,283, filed on Jan. 30, 2006.

(51) Int. Cl.
*A01H 5/00* (2006.01)

(52) U.S. Cl. ..... Plt./289

(58) Field of Classification Search ..... Plt./289
See application file for complete search history.

(56) References Cited

PUBLICATIONS

Royal Van Zanten Gardenmum Catalog 2002 listing variety 'Firecracker' at p. 8 with a photograph at p. 7. Catalog released Oct. 23, 2001.

Royal Van Zanten Catalog 2003 listing variety 'Firecracker' at pp. 21–22 with a photograph at p. 6. Catalog released Jan. 2, 2003.

Royal Van Zanten 2003–2004 "Pot plants and Bedding plants" Catalog listing variety 'Mermaid' with a photograph at p. 26 and variety 'Firecracker' with a photograph at p. 27. Catalog published Sep. 1, 2003.

*Primary Examiner*—Annette H Para
(74) *Attorney, Agent, or Firm*—Winston & Strawn, LLP

(57) ABSTRACT

A new variety of *Chrysanthemum* plant named 'Mermaid Yellow Improved', having a domed, round canopy of yellow decorative type flowers.

1 Drawing Sheet

Latin name of the genus and species: Botanical classification: *Chrysanthemum morifolium.*

Variety denomination: The new *Chrysanthemum* variety denomination is 'Mermaid Yellow Improved'.

BACKGROUND OF THE INVENTION

The present invention comprises a new and distinct cultivar of *Chrysanthemum* botanically known as *Chrysanthemum morifolium,* and referred to by the cultivar name 'Mermaid Yellow Improved'.

'Mermaid Yellow Improved' originated from a naturally occurring whole plant mutation grown in a controlled planting of the planting of the unpatented variety "Mermaid" in Chichester, West Sussex, United Kingdom.

The new variety 'Mermaid Yellow Improved' has been asexually reproduced by vegetative cuttings in Chichester, West Sussex, United Kingdom and the distinguishing characteristics are retained through successive generations of asexual reproduction.

BRIEF SUMMARY OF THE INVENTION

'Mermaid Yellow Improved' is a garden type of *Chrysanthemum* plant variety having a domed capitulum of yellow decorative type flowers.

Comparison with Original Cultivar

Plants of the new *Chrysanthemum* variety 'Mermaid Yellow Improved' are similar to the original cultivar 'Mermaid' in plant habit and growth rate. In side-by-side comparisons in Chichester, West Sussex, United Kingdom, under commercial practice, plants of the new *Chrysanthemum* variety 'Mermaid Yellow Improved' differed from plants of the original cultivar 'Mermaid' in the following characteristics:

1. The new variety 'Mermaid Yellow Improved' produces yellow decorative type flowers whereas the original cultivar 'Mermaid' produces white decorative type flowers.

Comparison with 'Firecracker'

Plants of the new *Chrysanthemum* variety 'Mermaid Yellow Improved' are dissimilar to plants of the unpatented variety 'Firecracker' in plant habit and growth rate. In side-by-side comparisons in Chichester, West Sussex, United Kingdom, under commercial practice, plants of the new *Chrysanthemum* variety 'Mermaid Yellow Improved' differed from plants of 'Firecracker' in the following characteristics:

1. The new variety 'Mermaid Yellow Improved' produces pale yellow decorative type flowers whereas 'Firecracker' produces golden yellow decorative type flowers.
2. Plants of the new variety 'Mermaid Yellow Improved' have larger and taller inflorescence than plants of 'Firecracker'.
3. Plants of the new variety 'Mermaid Yellow Improved' have a shorter natural season response time than plants of 'Firecracker'.

BRIEF DESCRIPTION OF ILLUSTRATIONS

Typical specimens of the plant and flowers for the new *Chrysanthemum* variety 'Mermaid Yellow Improved' are shown in the accompanying digital photograph, the colors shown are as true as possible within the usual limits of this kind of illustration. FIG. 1 is a whole plant view of the new variety 'Mermaid Yellow Improved' grown in a pot. The plant shown in the illustration and described below is 63 days from the commencement of planting outdoors natural season.

DETAILED BOTANICAL DESCRIPTION

The following description of the new *Chrysanthemum* variety, 'Mermaid Yellow Improved' is of plants grown outside, natural season, in Chichester, West Sussex, United Kingdom in the month of June. The cultivar has not been observed under all possible environmental conditions. The phenotype may vary significantly with variations in the environment such as temperature, length of day and light intensity, without any variance in genotype. The commercial classification of the new variety is a garden *Chrysanthemum.*

Plants of the new variety have been grown successfully under temperature conditions averaging about 50° F. at night and about 50° F. to 75° F. during the day. The plants were grown outdoors in 4 liter pots using a loamless compost. No growth retardants were used. To produce a commercial product, the plants may be pinched once with the center bud removed. The typical container size for commercial growth is 4 liters/8". It has been observed that the shelf life of the new variety is about 27 days with a response time of about 9 weeks natural season. The new variety is suitable for growth in a temperature range of about 50° F. to 75° F.

The new variety may be produced as a garden pot plant. The following description is with respect to a plant produced as pot *Chrysanthemum.* In the description of this new *Chrysanthemum* variety, color values have been taken from The Royal Horticultural Society Colour Chart (R.H.S.C.C.) by comparison to the new *Chrysanthemum* variety itself and may differ from the colors shown in the accompanying photograph.

Plant

Plant type: Pot.
Habit: Domed, free branching and spreading.
Height: 50 cm–60 cm.
Width: 50 cm–60 cm.
Stem:
- *Length.*—9 cm–12 cm.
- *Diameter.*—0.4 cm–0.7 cm.
- *Texture.*—Slightly pubescent.
- *Color.*—Near 152C.

Branching characteristics: Free branching and spreading.
Lateral branches:
- *Length.*—7 cm–15 cm.
- *Diameter.*—0.3 cm–0.6 cm.
- *Texture.*—slightly rough and slightly pubescent.

Number of Breaks from pinch.—6–11.
Response time: near 63 days natural season.
Vigor: Medium.
Shelf life: near 27 days.
Life of blooms: near 27 days.
Disease (susceptibility/resistance observed): None observed.
Pest (susceptibility/resistance observed): None observed.
Drought and temperature (susceptibility/resistance observed): None observed to date.
Growth retardant type and treatment: No treatment necessary. The plants were grown for 9 weeks in natural season conditions.
Propagation:
- *Type.*—Vegetative propagation via stem cuttings.
- *Time to rooting.*—12 days with soil temperatures of 70° F.
- *Rooting habit.*—After 7 Long Days (20 hours of light), the first roots emerge and form root primordia. In 12 Long Days, a complete root system is developed.

Foliage

Number of leaves per lateral branch: 6–10.
Compound or single: Single.
Arrangement of leaves: Alternate.
- *Shape of leaf.*—Typically 5 lobed ovate.
- *Size of leaf.*—Width: 2 cm–3.5 cm Length: 3 cm–5.5 cm.
- *Leaf apex.*—Acute.
- *Base.*—Obtuse.
- *Attachment.*—Petioled.
- *Aspect.*—Slightly undulating.
- *Margin.*—Palmately lobed.
- *Surface characteristics.*—Top: Smooth/slightly pubescent. Bottom: Slightly pubescent.

Petiole:
- *Color.*—Near 139A.
- *Length.*—0.6 cm–1.1 cm.
- *Diameter.*—0.2 cm–0.4 cm.
- *Surface.*—Slightly rough.

Venation: Net, prominent lateral and mid-vein at underside.
- *Color.*—Upper side: near 139C. Under side: Near 138C.

Color:
- *Mature leaf, upper side.*—near 147A; under side: near 147B. Young Leaf, upper side: near 147A; under side: near 147B.

Flower

Flower appearance: Matte.
Flower type: Decorative.
Flower form: Domed.
Flower shape: Round.
Flowering habit: Cyme.
Number of blossoms per branch: 6–9.
Typical and observed flowering season: September.
Inflorescence form: Corymbiform.
- *Depth of fully expanded blossoms.*—3 cm–4 cm.
- *Diameter of fully expanded blossoms.*—5 cm–7 cm.

Phyllaries:
- *Number.*—21–25.
- *Color.*—Near 138B.
- *Length.*—0.6 cm–0.9 cm.
- *Width.*—0.15 cm–0.3 cm.
- *Texture/Appearance.*—Shiny/slightly pubescent.

Peduncle: Peduncle length is shortest at the terminal flower and progressively longer moving down the stem; longest length is on average 12 cm, shortest length is on average 7 cm.
- *Length.*—7 cm–12 cm.
- *Diameter.*—0.2 cm–0.5 cm.
- *Angle from stem.*—Near 25°.
- *Color.*—Near 138C.
- *Surface.*—Slightly rough and pubescent.
- *Habit.*—slightly curving.
- *Strength.*—Strong.

Ray florets:
*Form/Shape.*—Straight slightly reflexing.
*Texture/Appearance.*—Matte.
*Number per flower.*—180–210.
*Length.*—1.5 cm–3.0 cm. Width: 0.3 cm–0.5 cm.
*Apex.*—Rounded.
*Base.*—Tubular.
*Margin.*—Entire.
Disc florets: No disc.
Fragrance: None.
Flower bud (at onset of color):
*Length.*—0.5 cm–0.8 cm.
*Diameter.*—0.8 cm–1 cm.
*Form/Shape.*—Round/Flattened.
General flower color:
1. *Ray florets, upper side.*—Immature: near 8A. Mature: near 8B. Older/Fading: near 8C.
2. *Ray florets, under side.*—Immature: near 8A. Mature: near 8B. Older/Fading: near 8C.
3. Disc florets: No disc florets.
4. Bud (at onset of color): near 181A.

Flower progression with age: Flowers fade very slowly with age.

Reproductive Organs

Gynoecium present on Ray florets.
Ray florets per individual flower: Pistillate.
*Pistil number.*—70–80 observed.
*Stigma color.*—Near 14D.
*Stigma shape.*—Forked.
*Style color.*—Near 144D.
*Style length.*—2.5 mm–3.5 mm.
Androecium: Not observed.
Fruit and seeds: None observed.

What is claimed is:

1. A new and distinct variety of *Chrysanthemum* plant, substantially as described and illustrated herein.

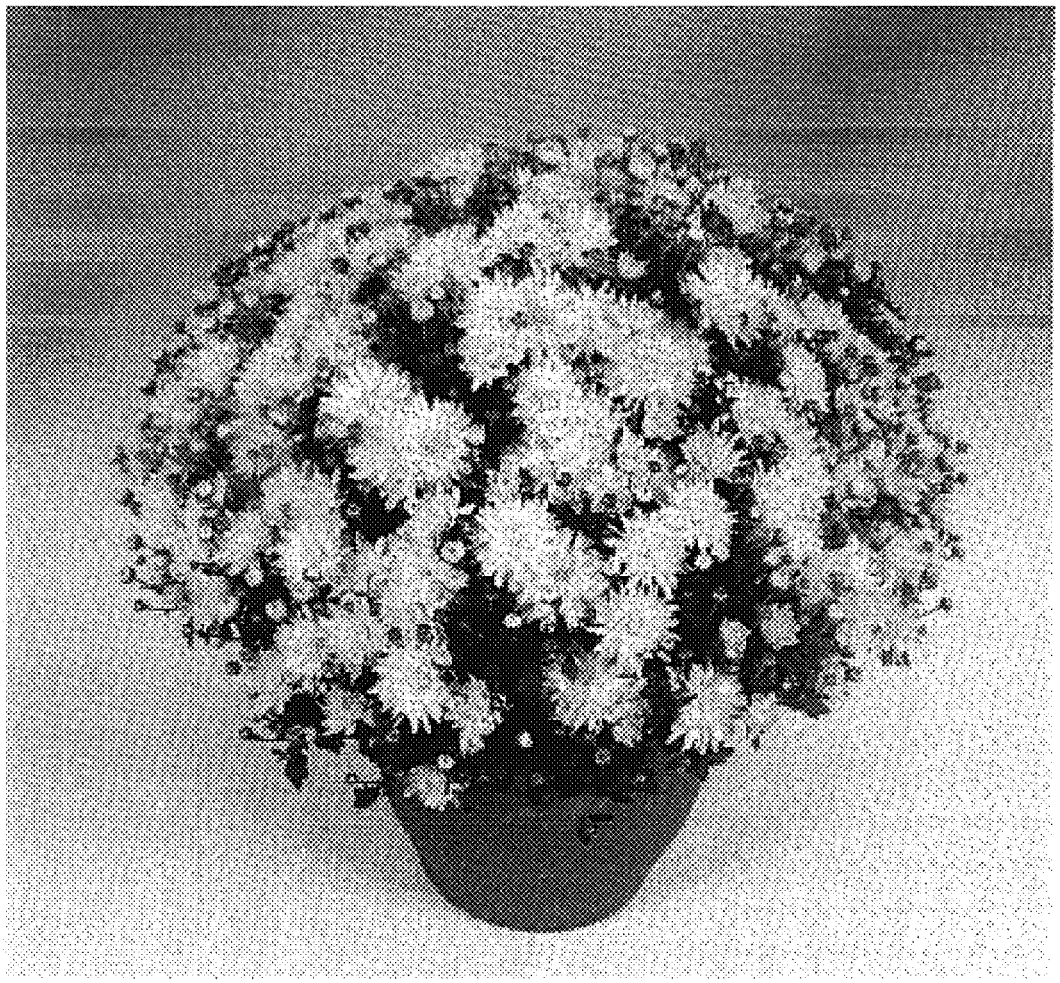

* * * * *